(12) United States Patent
Wang et al.

(10) Patent No.: US 10,488,319 B2
(45) Date of Patent: Nov. 26, 2019

(54) TESTING APPARATUS FOR GAS PERMEABILITY IN CONCRETE AND TESTING METHOD THEREFOR

(71) Applicant: TONGJI UNIVERSITY, Shanghai (CN)

(72) Inventors: Zhongping Wang, Shanghai (CN); Xiaoxu Ni, Shanghai (CN); Ronglong Sun, Shanghai (CN); Long Zhou, Shanghai (CN); Fei Cheng, Shanghai (CN)

( * ) Notice: Subject to any disclaimer, the term of this patent is extended or adjusted under 35 U.S.C. 154(b) by 245 days.

(21) Appl. No.: 15/803,767

(22) Filed: Nov. 4, 2017

(65) Prior Publication Data

US 2018/0058997 A1    Mar. 1, 2018

Related U.S. Application Data

(63) Continuation of application No. PCT/CN2015/081895, filed on Jun. 19, 2015.

(30) Foreign Application Priority Data

May 4, 2015    (CN) .......................... 2015 1 0225420

(51) Int. Cl.
*G01N 15/08* (2006.01)
*G01N 7/10* (2006.01)
*G01N 33/38* (2006.01)

(52) U.S. Cl.
CPC .......... *G01N 15/0826* (2013.01); *G01N 7/10* (2013.01); *G01N 33/383* (2013.01)

(58) Field of Classification Search
CPC ..... G01N 15/0826; G01N 7/10; G01N 33/383
USPC ........................................................ 73/38
See application file for complete search history.

(56) References Cited

FOREIGN PATENT DOCUMENTS

| CN | 1815174 A | 8/2006 |
|---|---|---|
| CN | 101358916 A | 2/2009 |
| CN | 201583477 U | 9/2010 |
| CN | 203299097 U | 11/2013 |
| DE | 3628955 A1 | 3/1988 |
| JP | 2014032125 | 2/2014 |
| SU | 759958 A1 | 8/1980 |

OTHER PUBLICATIONS

International Search Report of PCT/CN2015/081895 dated Feb. 15, 2016.

*Primary Examiner* — Justin Seo
*Assistant Examiner* — Rodney T Frank
(74) *Attorney, Agent, or Firm* — Erson IP (Nelson IP)

(57) ABSTRACT

An apparatus and method for testing gas permeability in concrete are provided. The apparatus is used for testing gas permeability of a concrete test sample, and includes a gas supply apparatus, an instrument body and a gas flow meter. The instrument body includes a frame body. A gas inlet ring, a gas outlet ring and a connection plate are successively arranged on the frame body from inside to outside. An input end of the gas inlet ring is connected with the gas supply apparatus, and an output end is connected with an input end of the gas outlet ring through the concrete test sample. An output end of the gas outlet ring is connected with the gas flow meter. The connection plate is connected with the concrete test sample.

9 Claims, 8 Drawing Sheets

TESTING APPARATUS FOR GAS PERMEABILITY IN CONCRETE AND TESTING METHOD THEREFOR

CROSS-REFERENCE TO RELATED APPLICATIONS

This application is a continuation of International Patent Application No. PCT/CN2015/081895 with a filing date of Jun. 19, 2015, designating the United States, now pending, and further claims priority to Chinese Patent Application No. 201510225420.4 with a filing date of May 4, 2015. The content of the aforementioned applications, including any intervening amendments thereto, are incorporated herein by reference.

FIELD OF THE INVENTION

The present invention relates to a concrete durability test technology, in particular to an apparatus and method for testing gas permeability in concrete.

BACKGROUND OF THE INVENTION

A research focus in current concrete academia is on improving the durability of the concrete and prolonging t he actual service life of the concrete. The key is to control permeability of the concrete. At present, the permeability performance of the concrete is represented by permeability coefficients of permeable media such as water, $O_2$, $N_2$, air and the like. According to test places, the test includes field tests and laboratory tests.

The Figg method and the Cembureau method are commonly used at present as permeability coefficient test methods which adopt gas as the permeable medium.

The Figg method can determine compactness of the concrete in a laboratory and a field environment and belongs to a semi-destructive method. During test, a pore of 10 mm is drilled in the surface of the concrete. The depth of the pore is about 40 mm. After float ash in t he pore is removed, a rubber plug tightly clinging to a wall of the pore is punched into the pore. A closed region is formed in a lower portion of the pore. Then a needle tube penetrates through the center of the rubber plug. The needle tube is externally connected with a vacuum pump with a valve. The closed region is vacuumed during test. The absolute pressure in the region is less than 0.45 MPa. The vacuum pump is turned off. Due to the leakage of concrete micropores, the vacuum degree is gradually decreased along with t he time. A measured index is the time spent when the absolute pressure in the closed region is changed from 0.45 MPa to 0.50 MPa, and the unit is second. Although equipment used in this method is simple, a sealing effect is not ideal. The reliability and reproducibility of test results are questioned by the academia.

In 1989, Kollek proposed the Cembureau method for determining the permeability coefficient of concrete by using $O_2$ as the permeable medium, which was widely accepted internationally. A principle of the Cembureau method is as follows: a stable air pressure is applied to a test sample; and a gas flow permeating the test sample under this pressure is recorded and then converted into the permeability coefficient which is used for comparing the permeability of the concrete. The method adopts a tire-type sealing structure. The sealing effect is very good, and test steps are also very strict. But this method still can only test the test sample in the laboratory, and cannot test the gas permeability of the concrete in the field environment. However, only the impermeability of a surface portion actually determines the field concrete durability. Therefore, the test result in the laboratory cannot completely reflect the actual impermeability and durability of the concrete.

Therefore, the research objective of those skilled in the art is to study a test method which is simple in operation, good in sealing effect, easy in carrying equipment, and capable of testing the gas permeability coefficient of the concrete in the field.

SUMMARY OF THE INVENTION

An objective of the present invention is to provide an apparatus for testing gas permeability in concrete convenient in field test and a test method thereof in order to overcome above defects of the prior art.

The objective of the present invention can be realized through the following technical solution:

An apparatus for testing gas permeability in concrete is used for testing gas permeability of a concrete test sample, and includes a gas supply apparatus, an instrument body and a gas flow meter. The instrument body includes a frame body. A gas inlet ring, a gas outlet ring and a connection plate are successively arranged on the frame body from inside to outside. An input end of the gas inlet ring is connected with the gas supply apparatus, and an output end is connected with an input end of the gas outlet ring through the concrete test sample. An output end of the gas outlet ring is connected with the gas flow meter. The connection plate is connected with the concrete test sample.

The gas supply apparatus supplies test gas of constant gas pressure to the instrument body. The test gas flows to the gas flow meter from the gas inlet ring successively via the concrete test sample and the gas outlet ring, and a gas permeability coefficient of the concrete is calculated according to the gas flow.

A bottom surface of the gas inlet ring is circular. A bottom surface of the gas outlet ring has a shape of a circular ring. A bottom area of the gas inlet ring is the same as the bottom area of the gas outlet ring.

An inner sealing ring is arranged between the gas inlet ring and the gas outlet ring, and an outer sealing ring is arranged between the gas outlet ring and the connection plate.

The gas supply apparatus includes a gas source, and a first gas transport channel, a second gas transport channel and a third transport channel with input ends being respectively connected with the gas source. An output end of the first gas transport channel is connected with the input end of the gas inlet ring; an output end of the second gas transport channel is connected with the input end of the inner sealing ring; and an output end of the third gas transport channel is connected with the input end of the outer sealing ring.

A test gas dehumidification apparatus is arranged'on a first gas transport pipe.

The gas source includes a relief valve, and a precision relief valve is arranged an the first gas transport pipe.

The instrument body also includes a plurality of fixing screw rods, and the connection plate is connected with the concrete test sample through the fixing screw rods.

A concrete gas permeability test method is characterized by including the following steps:

A, fixing an instrument body to a structural concrete test sample that reaches maturity, and inflating an inner sealing ring and an outer sealing ring until the internal pressure is 6 to 7 atmospheric pressures.

B, introducing test gas with the gas pressure constant at the test gas pressure into the gas inlet ring, recording a gas flow permeating the concrete test sample after the gas flow is stabilized, and calculating a permeability coefficient:

$$D = \frac{2QL\mu Pa}{A(P^2 - Pa^2)}$$

wherein D is a permeability coefficient, L is an effective permeation thickness, Q is the gas flow, u is gas viscosity, Pa is local atmospheric pressure, A is a permeable area, and P is the test gas pressure; and C, changing the test gas pressure, repeating the step B for three to five times, and calculating an average value of multiple measured permeability coefficients as a test value of the concrete test sample.

The effective permeation thickness L is:

$$L = \frac{\sqrt{2}}{2}\sqrt{R_3^2 + R_2^2} - \frac{\sqrt{2}}{2}R_1$$

Wherein $R_1$ is a radius of a bottom surface of the gas inlet ring, $R_2$ is a radius of an inner circle of a bottom surface of the gas outlet ring, and $R_3$ is a radius of an outer circle of the bottom surface of the gas outlet ring.

Compared with the prior art, the present invention has the following advantages:

1) With the test apparatus of the present invention, there is no need to take out the whole concrete test sample, and it only needs to connect the instrument body with a surface of the concrete test sample, thereby avoiding the cost for segmenting the concrete, greatly simplifying operation complexity, and facilitating the field test.

2) The sealing ring can guide the test gas to flow to the gas outlet ring from the gas inlet ring via the concrete test sample, thereby improving the precision of measuring the gas flow, and further improving the test precision, 3) The gas supply apparatus is divided into three gas transport channels, so that the stability of the pressure in the two sealing rings can be ensured while the test gas is supplied, and the situation that the pressure in the sealing rings is insufficient due to the long-time storage can be avoided.

4) The test gas dehumidification apparatus can heat the test gas, so that the concrete test sample is dried through the test gas.

5) The relief valve and the precision relief valve can adjust the test gas pressure, and can also ensure the pressure stability of the test gas entering the gas inlet ring, thereby completing the test.

In the figures: 1: concrete test sample; 3: instrument body; 4: gas flow meter; 25: diversion section; 26: diversion section; 211: relief valve; 212: liquid nitrogen cylinder tightening valve; 213: plastic connection hose; 214: liquid nitrogen cylinder; 215: gas filter; 216: safety valve; 221: test gas dehumidification apparatus; 222: precision relief valve; 223: stop-check valve; 224: stop-check valve; 225: diversion section; 231: stop-check valve; 241: stop-check valve; 31: gas inlet ring; 32: gas outlet ring; 33: connection plate; 34: inner sealing ring; 35: outer sealing ring; 36: frame body; 37: fixing screw rod; 38: gas inlet hole; 39: gas outlet hole; 341: gas inlet pipe of inner sealing ring; and 351: gas inlet pipe of outer sealing ring.

DETAILED DESCRIPTION OF THE EMBODIMENTS

The present invention is further described below in detail in combination with drawings and specific embodiments. The present embodiment is implemented on the premise of a technical solution of the present invention and gives detailed embodiments and a specific operation process, but the protection scope of the present invention is not limited to embodiments described below.

Embodiment 1

Figure 1:
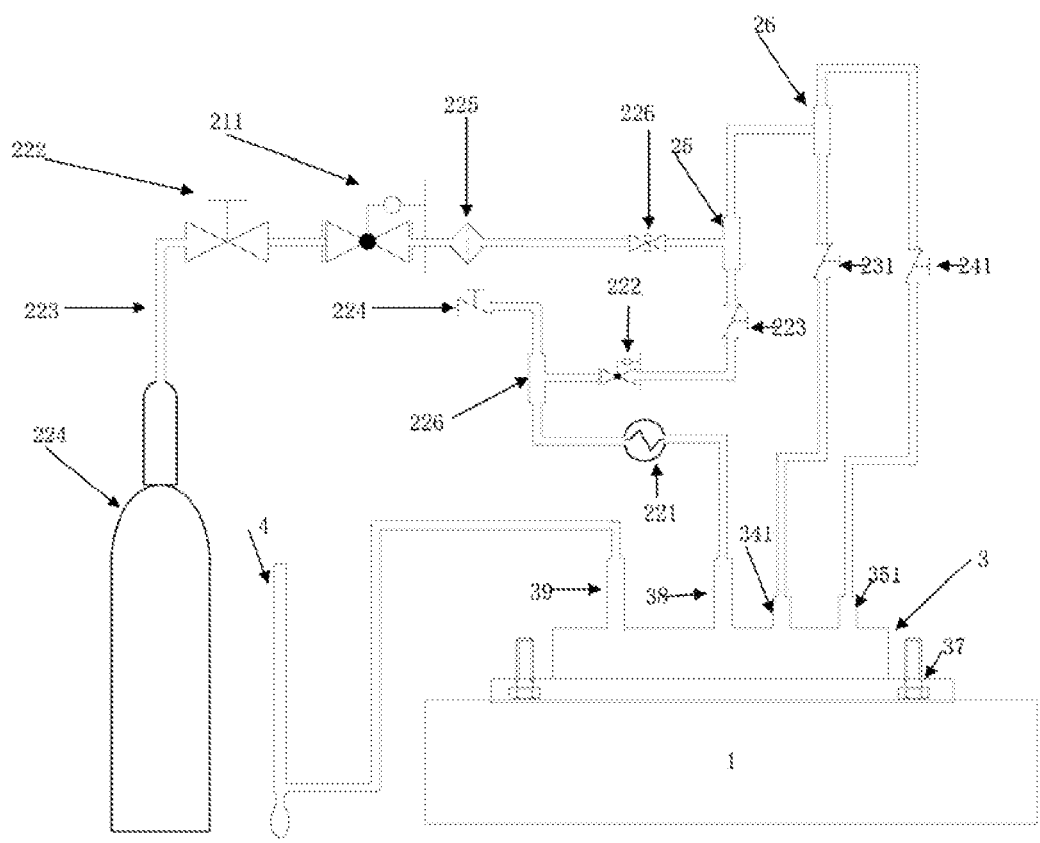
FIG. 1 is structural schematic diagram of the present invention.
Figure 2:
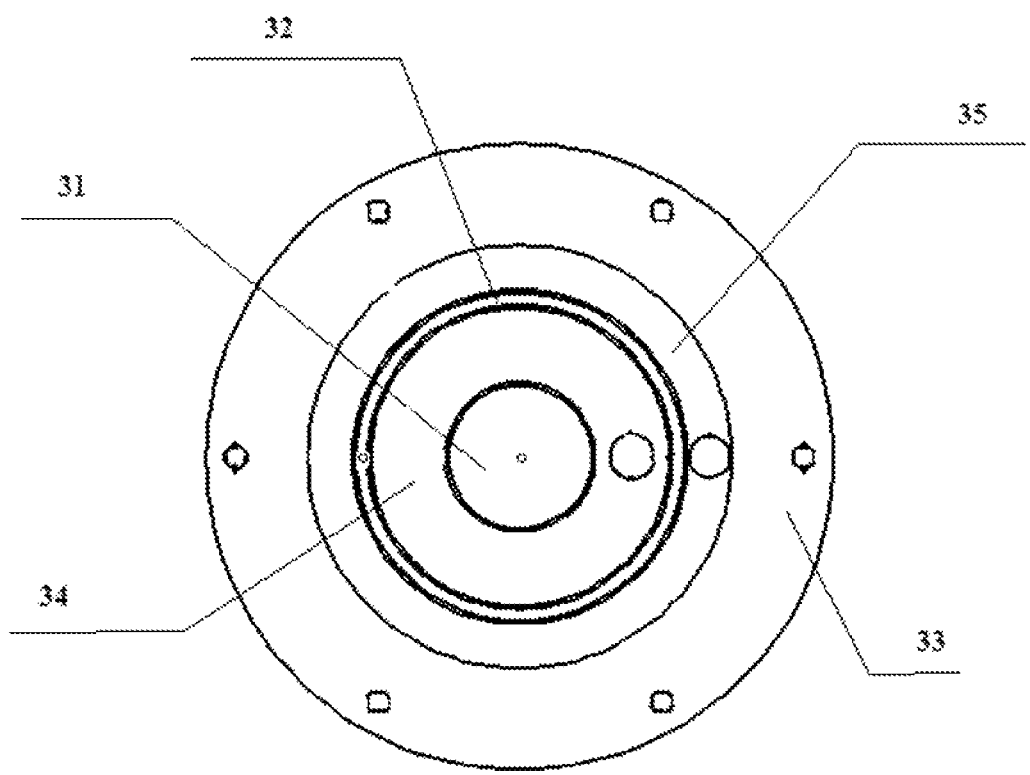
FIG. 2 is a schematic bottom view of an instrument body in embodiment 1 of the present invention.
Figure 3:
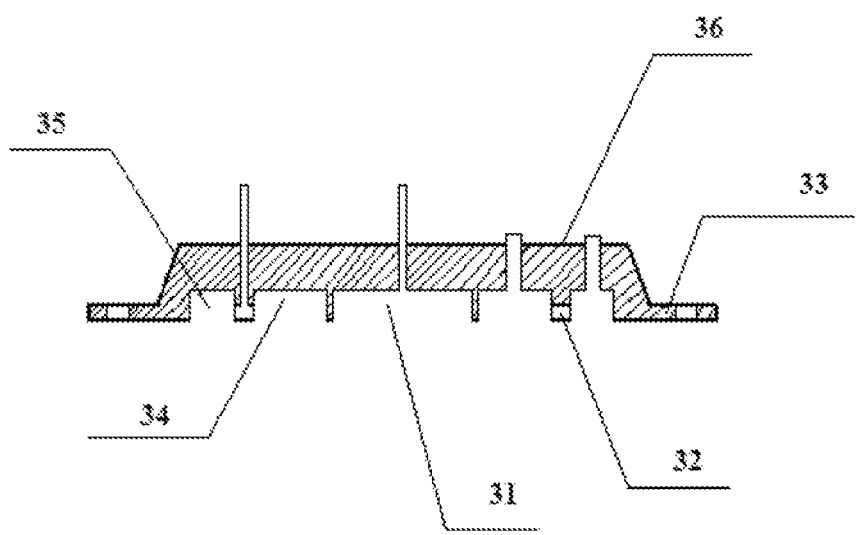
FIG. 3 is a schematic sectional view of an instrument body in embodiment 1 of t he present invention.

An apparatus for testing gas permeability in concrete is used for testing gas permeability of a concrete test sample 1. As shown in FIG. 1, the apparatus for testing gas permeability in concrete includes a gas supply apparatus, an instrument body 3 and a gas flow meter 4. As shown in FIG. 2 and FIG. 3, the instrument body 3 includes a frame body 36. A gas inlet ring 31, a gas outlet ring 32 and a connection plate 33 are successively arranged on the frame body 36 from inside to outside. The input end of the gas inlet ring 31 is connected with the gas supply apparatus 2, and the output end is connected with the input end of the gas outlet ring 32 through the concrete test sample 1. The output end of the gas outlet ring 32 is connected with the gas flow meter 4. The connection plate 33 is connected with the concrete test sample 1, wherein in the present embodiment, the gas flow meter 4 is a soap film flow meter.

The gas supply apparatus 2 supplies test gas to the instrument body 3. The test gas flows to the gas flow meter 4 from the gas inlet ring 31 successively via the concrete test sample 1 and the gas outlet ring 32, so that the concrete gas permeability coefficient is calculated according to the gas flow.

An inner sealing ring 34 is arranged between the gas inlet ring 31 and the gas outlet ring 32, and an outer sealing ring 35 is arranged between the gas outlet ring 32 and the connection plate 33.

As shown in FIG. 2, the inner sealing ring 34 is arranged between the gas inlet ring 31 and the gas outlet ring 32, and the outer sealing ring 35 is arranged between the gas outlet ring 32 and the connection plate 33.

The gas supply apparatus 2 includes a gas source 21, and a first gas transport channel 22, a second gas transport channel 23 and a third gas transport channel 24 with input ends being respectively connected with the gas source 21.

The output end of the first gas transport channel 22 is connected with the input end of the gas inlet ring 31; the output end of the second gas transport channel 23 is connected with the input end of the inner sealing ring 34; and the output end of the third gas transport channel 24 is connected with the input end of the outer sealing ring 35.

As shown in FIG. 1 and FIG. 2, a gas inlet hole 38 is formed in the center of the gas inlet ring 31; a gas outlet hole 39 is formed in the gas outlet ring 32; the first gas transport channel 22 is connected with the gas inlet ring 31 through the gas inlet hole 38; and the gas flow meter 4 is connected with the gas outlet ring 32 through the gas outlet hole 39.

Figure 4:
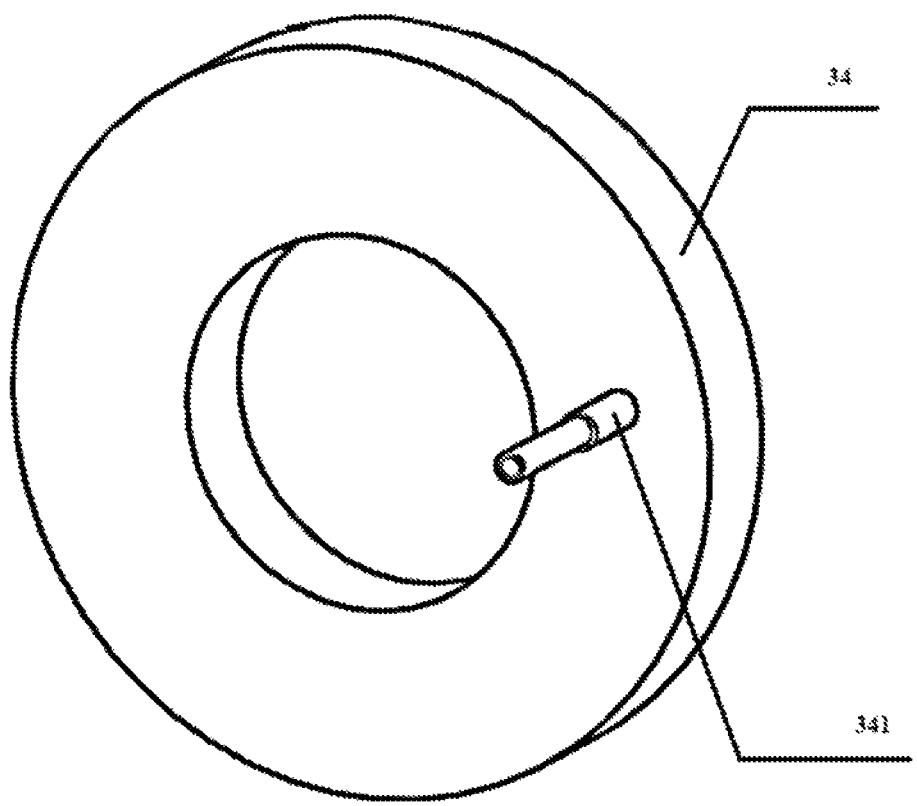
FIG. 4 is a structural schematic diagram of an inner sealing ring in embodiment 1 of the present invention.
Figure 5:
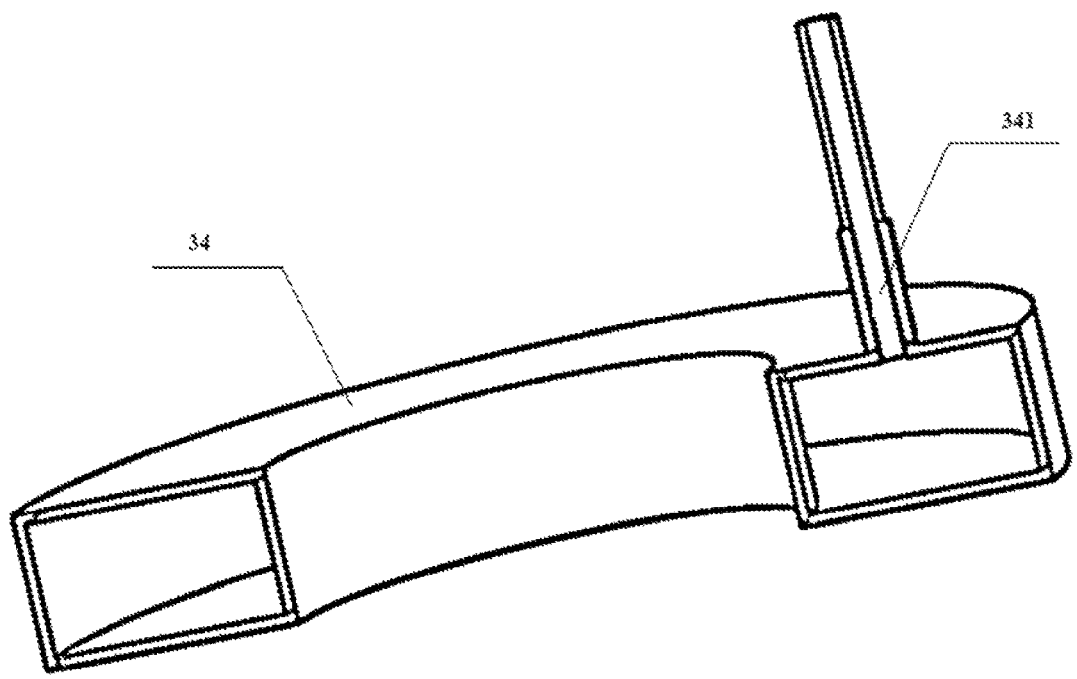
FIG. 5 is a three-dimensional schematic sectional view of an inner sealing ring in embodiment 1 of the present invention.

As shown in FIG. 1, FIG. 4 and FIG. 5, a gas inlet pipe 341 of inner sealing ring is arranged on the inner sealing ring 34, and the second gas transport channel 23 is connected with the inner sealing ring 34 through the gas inlet pipe 341 of the inner sealing ring; and the structure of the outer sealing ring 35 is similar to that of the inner sealing ring 34. As shown in FIG. 1, the third gas transport channel 24 is connected with the outer sealing ring 35 through a gas inlet pipe 351 of outer sealing ring.

A test gas dehumidification apparatus 221 is arranged on a first gas transport pipe 22.

The gas source 21 includes a relief valve 211, and a precision relief valve 222 is arranged on the first gas transport pipe 22.

The instrument body 3 also includes a plurality of fixing screw rods 37. The connection plate 33 is connected with the concrete test sample 1 through the fixing screw rods 37. A plurality of screw holes for the fixing screw rods 37 to pass through are formed in the connection plate 33. The quantity of the screw holes is consistent with the quantity of the fixing screw rods 37. In the present embodiment, the quantity of the fixing screw rods 37 and the quantity of the screw holes are respectively 6.

As shown in FIG. 1, in the present embodiment, the gas source 21 also includes a liquid nitrogen cylinder 214, a plastic connection hose 213, a liquid nitrogen cylinder tightening valve 212, a gas filter 215 and a safety valve 216. The liquid nitrogen cylinder 214, the plastic connection hose 213, the liquid nitrogen cylinder tightening valve 212, the relief valve 211, the gas filter 215 and the safety valve 216 are successively connected.

As shown in FIG. 1, the first gas transport channel 22 also includes two stop-check valves 223 and 224 as well as a diversion section 225, the stop-check valve 223, the precision relief valve 222, the diversion section 225 and the test gas dehumidification apparatus 221 are successively connected, the test gas dehumidification apparatus 221 is connected with the gas inlet hole 38, and the diversion section 225 is connected with the check-stop valve 224.

As shown in FIG. 1, the second gas transport channel 23 includes a stop-check valve 231. The third gas transport channel 24 includes a stop-check valve 241. The gas supply apparatus 2 also includes two diversion sections 25 and 26. The input end of the diversion section 25 is connected with the gas source 21. One output end of the diversion section 25 is connected with the stop-check valve 223, and the other output end of the diversion section 25 is connected with the input end of the diversion section 26. The input end of the diversion section 26 is correspondingly connected with the stop-check valve 231 and the stop-check valve 241 respectively.

The above apparatus for testing gas permeability in concrete is used for testing different concrete test samples 1 shown in Table 1.

TABLE 1

Mixing proportion of concrete for test

| Test No. | Water-cement ratio | Mixing proportion/kg | | | | Water reducing agent | $f_{c,28d}$/MPa |
|---|---|---|---|---|---|---|---|
| | | Water | Cement | Sand | Stone | | |
| 1 | 0.58 | 212 | 365 | 691 | 1129 | | 29.4 |
| 2 | 0.55 | 201 | 365 | 675 | 1150 | | 34.5 |
| 3 | 0.52 | 190 | 365 | 609 | 1236 | | 36.6 |
| 4 | 0.42 | 152 | 365 | 609 | 1236 | 3.65 | 42.9 |

The test specifically includes the following steps:

A, closing all stop-check valves as well as a relief valve 211, a precision relief valve 222, a liquid nitrogen cylinder tightening valve 212 and a safety valve 216; drilling six holes in a concrete test sample 1 reaching maturity by using a percussion drill according to positions of screw holes of an instrument body 3; burying fixing screw rods 37 into the concrete by utilizing a quick-hardening binder; aligning the instrument body 3 with the screw rods; and tightening screw caps to allow the instrument body 3 to tightly contact the concrete test sample 1; and during test, firstly opening the stop-check valve 231 and the stop-check valve 241, then opening the liquid nitrogen cylinder tightening valve 212 and the relief valve 211, and adjusting the relief valve 211 to inflate the inner sealing ring 34 and the outer sealing ring 35 until the internal pressure reaches 6 to 7 atmospheric pressures;

B, closing the stop-check valve 231 and the stop-check valve 241, opening the stop-check valve 223 and the test gas dehumidification apparatus 221, adjusting the precision relief valve 222 to enable the pressure of the test gas entering the instrument body 3 to be 0.1 MPa, recording, by a gas flow meter 4, the gas flow permeating the concrete test sample 1 after the gas flow is stabilized, and calculating the permeability coefficient:

$$D = \frac{2QL\mu Pa}{A(P^2 - Pa^2)}$$

wherein D is the permeability coefficient, L is an effective permeation thickness, Q is the gas flow, u is gas viscosity, Pa is a local atmospheric pressure, A is permeable area, and P is test gas pressure; and the effective permeation thickness L is:

$$L = \frac{\sqrt{2}}{2}\sqrt{R_3^2 + R_2^2} - \frac{\sqrt{2}}{2}R_1$$

wherein $R_1$ is a radius of a bottom surface of the gas inlet ring, $R_2$ is a radius of an inner circle of a bottom surface of the gas outlet ring, and $R_3$ is a radius of an outer circle of the bottom surface of the gas outlet ring.

Specifically, $L=L_1+_2+L_3$

Figure 6:
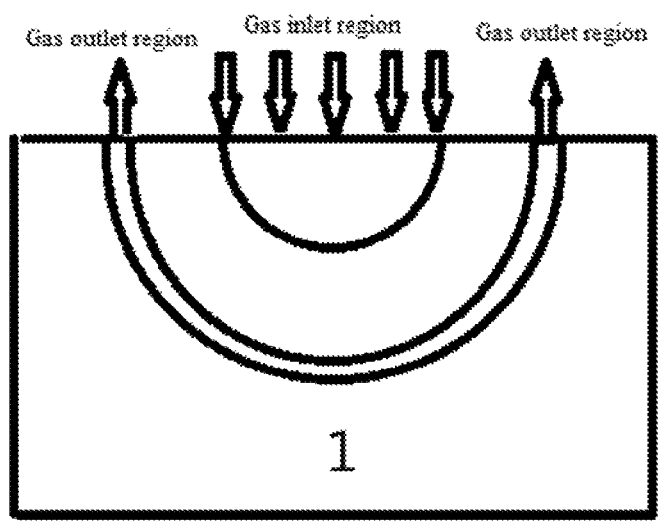
FIG. 6 is a schematic diagram of a motion path of test gas on a surface layer of a concrete test sample.
Figure 8:
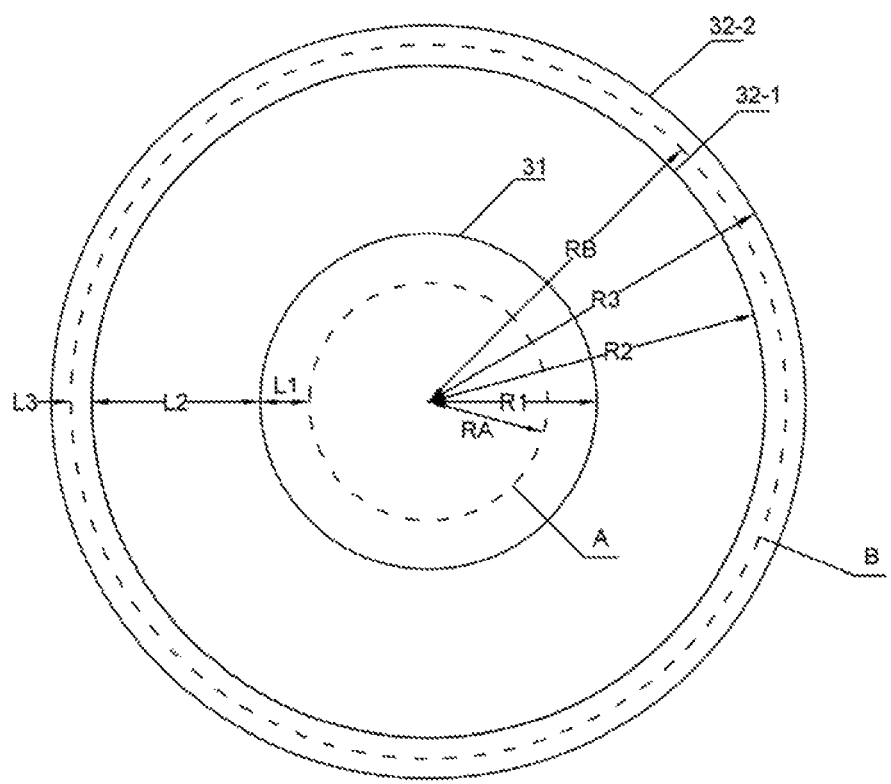
FIG. 8 is a schematic diagram of a permeation thickness calculation process.

As shown in FIG. 6 and FIG. 8: $R_1$ is the radius of the bottom surface of the gas inlet ring 31, $R_2$ is the radius of the inner circle 32-1 of the bottom surface of the gas outlet ring, $R_3$ is the radius of the outer circle 32-2 of the bottom surface of the gas outlet ring. In the present embodiment, $R_1$ is 50 mm, $R_2$ is 100 mm, $R_3$ is 112 mm. The permeation of the gas from the gas inlet ring 31 can be equivalent to the permeation from a circumference of a circle A. The circle A is concentric with the gas inlet ring 31, and an area is equal to half of the gas inlet area 31. Similarly, the permeation of the gas from the gas outlet ring 32 can be equivalent to the permeation from the circumference of the circle B, and the area of the gas inlet ring 32 is equally divided by the circle B. $L_1$ is a difference between the radius $R_1$ of the gas inlet ring 31 and the radius $R_A$ of the circle A, and a calculation process is as follows:

$$L_1 = \left(1 - \frac{\sqrt{2}}{2}\right) R_1$$

$L_2$ is a thickness of the sealing ring. A calculation process is $L_2 = R_2 - R_1$. $L_3$ is a difference between the radius $R_B$ of the circle B and the radius $R_2$ of the inner circle of the bottom surface of the gas outlet ring. The calculation process is:

$$L_3 = \frac{\sqrt{2}}{2}\sqrt{R_3^2 + R_2^2} - R_2$$

When the quantity of the gas permeated from the interior of the concrete test sample 1 is greater than 90% of the quantity of the gas entering the concrete test sample 1 (under the condition that an error is 10%), the test data is considered to be valid.

C, Changing the test gas pressure to be 0.2 MPa and 0.3 MPa respectively, repeating the step B, and measuring the gas flow under various conditions. The test data is shown in Table 2.

TABLE 2

Summary of concrete permeating gas flow rates Unit: ml/min

| Test No. | Water-cement ratio | Test gas pressure P (MPa) | | |
|---|---|---|---|---|
| | | P = 0.1 | P = 0.2 | P = 0.3 |
| 1 | 0.58 | 171.4 | 447.8 | 900.8 |
| 2 | 0.55 | 123.2 | 324.3 | 618.6 |
| 3 | 0.52 | 59 | 155.4 | 300 |
| 4 | 0.42 | 16.4 | 39.7 | 73 |

The gas permeability coefficient values of the tested sample under the permeation pressure of 0.1 MPa, 0.2 MPa and 0.3 MPa are obtained; and a test result is shown in Table 3.

TABLE 3

Summary of concrete permeabflity coefficient results Unit: ×10$^{-15}$ m$^2$

| Test No. | Water-cement ratio | P = 0.1 MPa | P = 0.2 MPa | P = 0.3 MPa | Average value |
|---|---|---|---|---|---|
| 1 | 0.58 | 3.15 | 3.09 | 3.31 | 3.18 |
| 2 | 0.55 | 2.27 | 2.24 | 2.28 | 2.26 |
| 3 | 0.52 | 1.09 | 1.07 | 1.10 | 1.09 |
| 4 | 0.42 | 0.30 | 0.27 | 0.27 | 0.28 |

An average value of multiple obtained permeability coefficients is calculated as a test value of the concrete test sample 1.

Embodiment 2

Similarities in the present embodiment to embodiment are not repeated herein, and only the difference is described.

Figure 7:
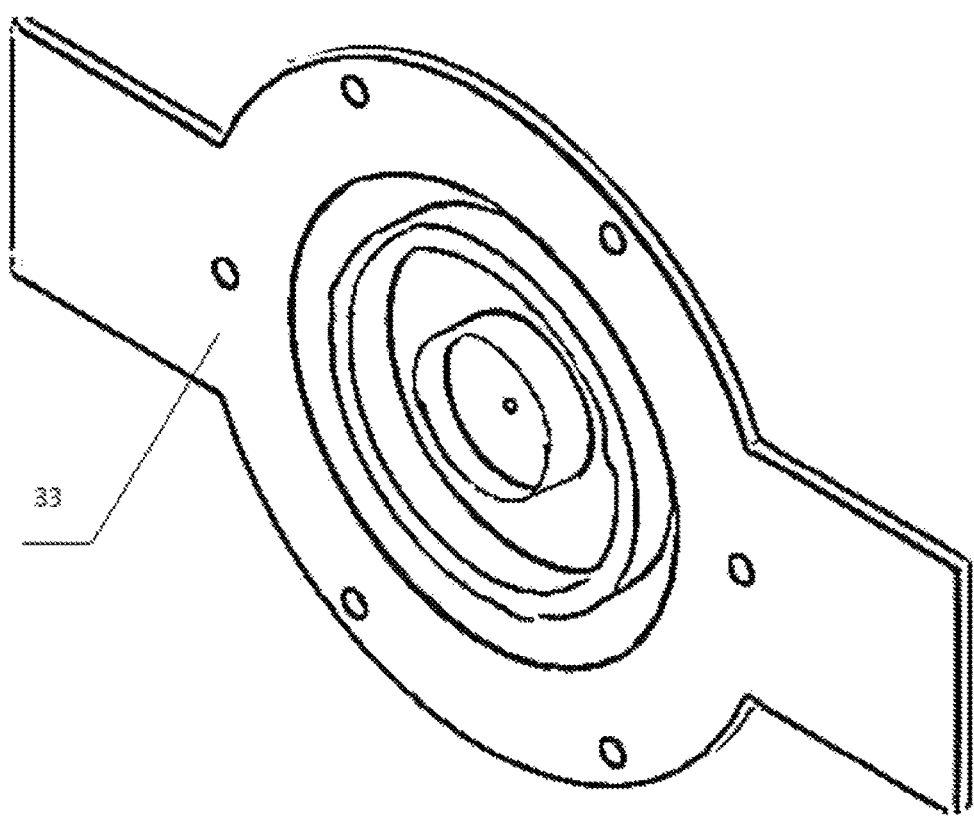
FIG. 7 is a structural schematic diagram of an instrument body in embodiment 2 of the present invention.

The present embodiment significantly differs from embodiment 2 in the shape of the connection plate 33. As shown in FIG. 7, in the present embodiment, bulges for connecting hoops are arranged on both sides of the connection plate 33. In the case that the concrete test samples 1 are a beam and a column, the instrument body 3 of the present embodiment is used and fixed by virtue of the hoops.

We claim:

1. An apparatus for testing gas permeability in concrete, which is used for testing gas permeability of a concrete test sample (1), comprising: a gas supply apparatus (2), an instrument body (3), and a gas flow meter (4), wherein the instrument body (3) comprises a frame body (36); a gas inlet ring (31), a gas outlet (32) and a connection plate (33) are successively arranged on the frame body (36) from inside to outside; an input end of the gas inlet ring (31) is connected with the gas supply apparatus (2); an output end is connected with an input end of the gas outlet ring (32) through the concrete test sample (1); the output end of the gas outlet ring (32) is connected with the gas flow meter (4); and the connection plate (33) is connected with the concrete test sample (1); and the gas supply apparatus (2) supplies test gas of constant gas pressure to the instrument body (3); the test gas flows to the gas flow meter (4) from the gas inlet ring (31) successively via the concrete test sample (1) and the gas outlet ring (31); and then a gas permeability coefficient of the concrete is calculated according to a gas flow.

2. The apparatus for testing gas permeability in concrete according to claim 1, wherein a bottom surface of the gas inlet ring (31) is circular; a bottom surface of the gas outlet ring (32) has a shape of a circular ring; and a bottom area of the gas inlet ring (31) is the same as the bottom area of the gas outlet ring (32).

3. The apparatus for testing gas permeability in concrete according to claim 1, wherein an inner sealing ring (34) is arranged between the gas inlet ring (31) and the gas outlet ring (32), and an outer sealing ring (35) is arranged between the gas outlet ring (32) and the connection plate (33).

4. The apparatus for testing gas permeability in concrete according to claim 3, wherein the gas supply apparatus (2) comprises a gas source (21), and a first gas transport channel (22), a second gas transport channel (23) and a third gas transport channel (24) with input ends being respectively connected with the gas source (21); an output end of the first gas transport channel (22) is connected with the input end of the gas inlet ring (31); an output end of the second gas transport channel (23) is connected with the input end of the inner sealing ring (34); and the output end of the third gas transport channel (24) is connected with the input end of the outer sealing ring (35).

5. The apparatus for testing gas permeability in concrete according to claim 4, wherein a test gas dehumidification apparatus (221) is arranged on the first gas transport pipe (22).

6. The apparatus for testing gas permeability in concrete according to claim 4, wherein the gas source (21) comprises a relief valve (211), and a precision relief valve (222) is arranged on the first gas transport pipe (22).

7. The apparatus for testing gas permeability in concrete according to claim wherein the instrument body (3) further comprises a plurality of fixing screw rods (37), and the connection plate (33) is connected with the concrete test sample (1) through the fixing screw rods (37).

8. A test method of the apparatus for testing gas permeability in concrete according to claim 1, comprising the steps:

A, fixing an instrument body (3) to a structural concrete test sample (1) reaching maturity, and inflating an inner sealing ring (34) and an outer sealing ring (35) until the internal pressure reaches 6 to 7 atmospheric pressures;

B, introducing test gas with the gas pressure constant at the test gas pressure into the gas inlet ring (31), recording a gas flow permeating the concrete test sample (1) after the gas flow is stabilized, and calculating a permeability coefficient:

$$D = \frac{2QL\mu Pa}{A(P^2 - Pa^2)}$$

wherein is the permeability coefficient, L is an effective permeation thickness, Q is gas flow, u is gas viscosity, Pa is local atmospheric pressure, A is permeable area, and P is the test gas pressure; and C, changing the test gas pressure, repeating the step B for three to five times, and calculating an average value of multiple measured permeability coefficients as a test value of the concrete test sample (1).

9. The test method according to claim 8, wherein an effective permeation thickness L is:

$$L = \frac{\sqrt{2}}{2}\sqrt{R_3^2 + R_2^2} - \frac{\sqrt{2}}{2}R_1$$

wherein $R_7$ is a radius of a bottom surface of the gas inlet ring, $R_2$ is a radius of an inner circle of a bottom surface of the gas outlet ring, and $R_3$ is a radius of an outer circle of the bottom surface of the gas outlet ring.

* * * * *